(12) United States Patent
Georgeson

(10) Patent No.: US 9,594,033 B2
(45) Date of Patent: Mar. 14, 2017

(54) VISIBLE X-RAY INDICATION AND DETECTION SYSTEM FOR X-RAY BACKSCATTER APPLICATIONS

(71) Applicant: The Boeing Company, Chicago, IL (US)

(72) Inventor: Gary E. Georgeson, Tacoma, WA (US)

(73) Assignee: THE BOEING COMPANY, Chicago, IL (US)

( * ) Notice: Subject to any disclaimer, the term of this patent is extended or adjusted under 35 U.S.C. 154(b) by 93 days.

(21) Appl. No.: 14/338,322

(22) Filed: Jul. 22, 2014

(65) Prior Publication Data

US 2016/0025658 A1 Jan. 28, 2016

(51) Int. Cl.
| | |
|---|---|
| *G01N 23/203* | (2006.01) |
| *G01T 1/10* | (2006.01) |
| *G01T 1/20* | (2006.01) |
| *G01N 23/207* | (2006.01) |
| *G01T 1/04* | (2006.01) |
| *G01T 1/16* | (2006.01) |

(52) U.S. Cl.
CPC ....... *G01N 23/203* (2013.01); *G01N 23/2076* (2013.01); *G01T 1/04* (2013.01); *G01T 1/10* (2013.01); *G01T 1/16* (2013.01); *G01T 1/20* (2013.01)

(58) Field of Classification Search
CPC ...... G01N 23/10; G01N 23/203; G01N 23/22; G01N 23/223; G01T 1/20
USPC ................................ 378/44–50, 86–90, 98.7
See application file for complete search history.

(56) References Cited

U.S. PATENT DOCUMENTS

| | | | | |
|---|---|---|---|---|
| 5,181,234 A | * | 1/1993 | Smith .................. | G01V 5/0025 250/472.1 |
| 5,696,806 A | * | 12/1997 | Grodzins ............. | G01N 23/046 378/86 |
| 5,832,054 A | * | 11/1998 | Kuwabara ............ | G01N 23/223 378/45 |
| 5,940,468 A | * | 8/1999 | Huang .................. | G01N 23/04 378/57 |
| 6,151,381 A | * | 11/2000 | Grodzins ............... | G01N 23/04 378/57 |
| 6,175,614 B1 | * | 1/2001 | Jensen ..................... | H05G 1/36 378/95 |

(Continued)

FOREIGN PATENT DOCUMENTS

| | | |
|---|---|---|
| JP | 2011056131 A | 3/2011 |
| WO | WO2013184204 A2 | 12/2013 |
| WO | WO2013184204 A9 | 1/2014 |

OTHER PUBLICATIONS

Seth Coe-Sullivan et al., "Large-Area Ordered Quantum-Dot Monolayers via Phase Separation During Spin-Casting," Advanced Functional Materials 2005, vol. 15, pp. 1117-1124.*

(Continued)

*Primary Examiner* — Allen C. Ho
(74) *Attorney, Agent, or Firm* — Yee & Associates, P.C.

(57) ABSTRACT

An X-ray backscatter indication and detection system, including an object disposed with respect to a target area targeted by X-rays, such that X-rays that backscatter from the target area strike the surface of the object. The surface of the object includes an X-ray sensitive indicator substance that fluoresces with a visible light when contacted by backscattered X-rays.

20 Claims, 9 Drawing Sheets

(56) References Cited

U.S. PATENT DOCUMENTS

| | | | | |
|---|---|---|---|---|
| 6,192,104 B1* | 2/2001 | Adams | G01N 23/203 | 378/149 |
| 6,249,567 B1* | 6/2001 | Rothschild | G01N 23/20 | 378/63 |
| 6,556,653 B2* | 4/2003 | Hussein | G01N 23/02 | 378/57 |
| 6,621,888 B2* | 9/2003 | Grodzins | G01N 23/20 | 378/57 |
| 6,665,373 B1* | 12/2003 | Kotowski | G01N 23/20 | 378/57 |
| 6,754,304 B1* | 6/2004 | Kumakhov | G01N 23/223 | 378/45 |
| 6,785,360 B1* | 8/2004 | Annis | A61B 6/032 | 378/137 |
| 7,020,238 B1* | 3/2006 | Kantonen | G01N 23/223 | 378/102 |
| 7,110,493 B1* | 9/2006 | Kotowski | G01V 5/0025 | 378/57 |
| 7,400,701 B1* | 7/2008 | Cason | G01V 5/0025 | 378/57 |
| 7,409,037 B2* | 8/2008 | Puusaari | G01N 23/223 | 378/44 |
| 7,428,293 B2* | 9/2008 | Fukai | G01N 23/223 | 378/147 |
| 7,443,951 B2* | 10/2008 | Kenning | G01N 23/223 | 378/102 |
| 7,623,625 B2* | 11/2009 | Boyden | G01N 23/201 | 378/86 |
| 7,688,942 B2* | 3/2010 | Klein | G01N 23/223 | 250/400 |
| 7,796,733 B2* | 9/2010 | Hughes | G01T 1/167 | 378/57 |
| 7,809,109 B2* | 10/2010 | Mastronardi | G01N 23/201 | 378/146 |
| 7,826,589 B2* | 11/2010 | Kotowski | G01V 5/0025 | 378/57 |
| 7,902,524 B2 | 3/2011 | Safai et al. | | |
| 7,925,452 B2 | 4/2011 | Safai et al. | | |
| 8,199,996 B2* | 6/2012 | Hughes | G01V 5/0025 | 378/87 |
| 8,442,186 B2* | 5/2013 | Rothschild | G01V 5/0025 | 378/57 |
| 8,693,627 B2* | 4/2014 | Oyaizu | C09K 11/7733 | 250/483.1 |
| 8,761,338 B2* | 6/2014 | Safai | G01N 23/203 | 378/197 |
| 8,816,287 B2* | 8/2014 | Weinberg | G01T 1/16 | 250/370.01 |
| 8,816,291 B2* | 8/2014 | Hawver | G01N 23/203 | 250/370.09 |
| 8,855,268 B1* | 10/2014 | Safai | G01N 23/203 | 378/130 |
| 8,879,688 B2* | 11/2014 | Safai | G01N 23/203 | 378/86 |
| 8,975,112 B2* | 3/2015 | Fürst | H01L 51/0004 | 257/40 |
| 9,031,188 B2* | 5/2015 | Belcher | G01N 23/203 | 378/58 |
| 9,036,781 B1* | 5/2015 | Safai | G01N 23/00 | 378/86 |
| 9,057,679 B2* | 6/2015 | Morton | G01N 23/04 | |
| 9,123,450 B2* | 9/2015 | Liesenfelt | G21K 1/04 | |
| 9,151,668 B1* | 10/2015 | Nagarkar | G01J 1/42 | |
| 9,151,721 B2* | 10/2015 | Safai | G01N 23/203 | |
| 2008/0233658 A1* | 9/2008 | Marshall | G01N 21/6408 | 436/172 |

OTHER PUBLICATIONS

Kang et al., "CdTe quantum dots and polymer nanocomposites for x-ray scintillation and imaging," Applied Physics Letters, vol. 98, No. 18, May 2011, pp. 181914-1-181914-3.

Extended European Search Report, dated Dec. 18, 2015, regarding Application No. EP15171621.4, 8 pages.

Baharin et al., "Development of an ionising radiation detector based on quantum dots absorbed in porous glass," 2012 12th IEEE International Conference on Nanotechnology, Aug. 20-23, 2012, 8 pages.

* cited by examiner nited States Patent

VISIBLE X-RAY INDICATION AND DETECTION SYSTEM FOR X-RAY BACKSCATTER APPLICATIONS

BACKGROUND INFORMATION

1. Field

The present disclosure relates to the indication, detection and characterization of X-rays, and more particularly to backscattered X-rays.

2. Background

X-rays are an energetic form of light the human eye cannot see. As is well known, X-rays have many useful applications, such as in medicine, dentistry, and scientific research.

However, because X-rays are so energetic, they are difficult to detect without using expensive, advanced equipment. Similarly, quantitatively characterizing a flux of X-rays usually requires expensive, advanced equipment. Thus, new and improved techniques for detecting and characterizing X-rays are desirable, particularly for backscattered X-rays. Backscattered X-rays are X-rays that strike a target area and then scatter from the target area, potentially striking one or more additional areas other than the target.

SUMMARY

The illustrative embodiments provide for a number of different implementations. For example, the illustrative embodiments provide for an X-ray backscatter indication and detection system, including an object disposed with respect to a target area targeted by X-rays, such that X-rays that backscatter from the target area strike the surface of the object. The surface of the object includes an X-ray sensitive indicator substance that fluoresces with a visible light when contacted by backscattered X-rays.

The illustrative embodiments also provide for an X-ray leak detector. The detector includes an X-ray generator, a target area disposed such that X-rays generated by the X-ray generator strike the target area, and a shield disposed in front of the X-ray generator. The shield is configured to block X-rays backscattered from the target area. The detector also includes a first panel disposed behind the shield relative to the target area. An X-ray fluorescent Q-dot solution is disposed on the first panel, the X-ray fluorescent Q-dot solution configured to fluoresce with a visible light when X-rays strike the X-ray fluorescent Q-dot solution.

The illustrative embodiments also provide for a method. The method includes inspecting an article, having an X-ray fluorescent Q-dot solution disposed on at least a portion of the article. The X-ray fluorescent Q-dot solution is configured to fluoresce a visible light when X-rays strike the X-ray fluorescent Q-dot solution. Inspecting includes determining whether the X-ray fluorescent Q-dot solution is fluorescing.

The illustrative embodiments also provide for an article. The article includes an object comprising a surface and an X-ray fluorescent Q-dot solution disposed on the surface. The X-ray fluorescent Q-dot solution is configured to fluoresce with a visible light when X-rays strike the X-ray fluorescent Q-dot solution. The X-ray fluorescent Q-dot solution is placed on the surface in a pattern selected from the group consisting of: a word, alphanumeric characters, and an image.

The illustrative embodiments also provide for an X-ray monitor. The monitor includes an X-ray measuring tool comprising a housing, a sensor target area on the housing and configured to receive an X-ray flux, and an X-ray detector disposed inside the housing and configured to measure the X-ray flux. The monitor also includes an X-ray fluorescent Q-dot solution disposed on the sensor target area, the X-ray fluorescent Q-dot solution configured to fluoresce with a visible light when X-rays strike the X-ray fluorescent Q-dot solution.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

Figure 1:
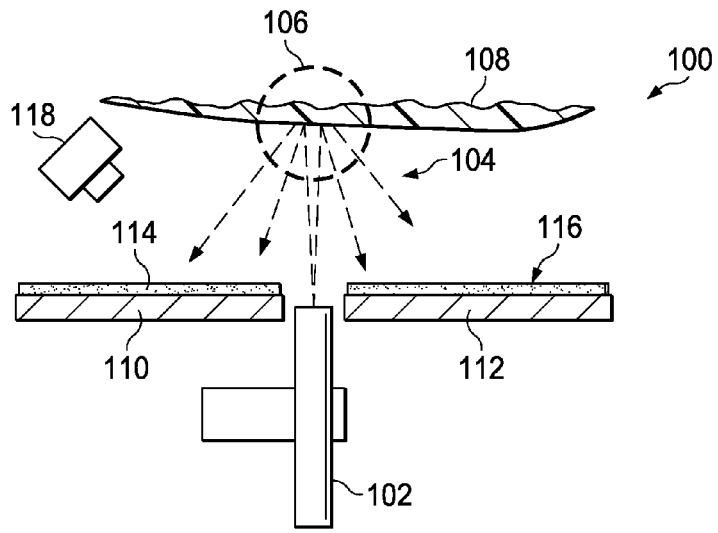
FIG. 1 illustrates a side view of an X-ray backscatter indication and detection system, in accordance with an illustrative embodiment.

The illustrative embodiments provide several useful functions. For example, the illustrative embodiments recognize and take into account that inexpensively detecting X-rays, including backscattered X-rays, remains challenging. The illustrative embodiments also recognize and take into account that a mechanism for detecting the presence of X-rays with an indicator in the visible spectrum of light would allow for rapid reaction to the presence of X-rays. The illustrative embodiments also recognize and take into account that the presence and distribution of X-rays indicated using visible light will allow ordinary visible light cameras to guide and control X-ray related equipment, including X-ray generators, X-ray targets, X-ray monitors, and the like.

As used herein, "X-rays", like visible light, are photons, a form of electromagnetic radiation. X-rays have a wavelength in the range of about 0.01 nanometers to about 10 nanometers, corresponding to frequencies in the range of about 30 petahertz ($3 \times 10^{16}$ Hz) to about 30 exahertz ($3 \times 10^{19}$ Hz), and to energies in the range of about i0 {electron volts (eV) to about i00 kilo electron volts (KeV).

Electromagnetic radiation includes ordinary visible light. However, electromagnetic radiation includes many energies of photons, with visible light being a small range of energies along the entire electromagnetic spectrum. If the range of the electrometric spectrum were arranged along a straight line in order of energy, then radio waves would be at the far right, followed by microwaves, then infrared light, then visible light, then ultraviolet light, then X-rays, and then gamma rays. Photons behave as both particles and as waves, being characterizable as a packet of waves. Waves may be described as having a wavelength, an amplitude, and a frequency; thus, photons, including visible light, may be characterized as having a wavelength and a frequency. The less energetic the photon the longer the wavelength, and conversely the more energetic the photon the shorter the wavelength. Likewise, the less energetic the photon the lower the frequency, and conversely the more energetic the photon the faster the frequency.

As used herein, "fluorescence" refers to the emission of an emission photon by a substance that has absorbed a different frequency of an incident photon striking the substance. Fluorescence is a form of luminescence. Fluorescence occurs as a result of molecules or atoms increasing energy states because of the incident photons, followed by a decreased energy state that causes the molecules or atoms to emit the fluorescent light. Fluorescence may also occur as a result of different excitation techniques, such as fluorescence resulting from a bombardment of energetic electrons. The illustrative embodiments may also be applied to these other types of fluorescence.

In most cases, the emitted light of fluorescence has a longer wavelength and is less energetic than the incident, absorbed light. In some cases, such as in double photon absorption, the emitted light from fluorescence may have the same or shorter wavelength as the absorbed light, and has the same energy or is more energetic than the absorbed light. However, the illustrative embodiments described herein primarily refer to single photon absorption and lower energy emission photons. Specifically, the illustrative embodiments described herein primarily refer to fluorescence of visible light resulting from the absorption of X-rays.

As indicated above, X-rays are invisible to the human eye, so users of X-ray equipment typically use expensive, specialized sensors or monitors to indicate the presence of X-rays. Users of X-ray equipment may also wear film badges that show that X-ray exposure has taken place. However, such badges only detect the past presence of X-rays and typically produce an insufficient quantitative characterization of an X-ray flux striking such badges.

Quantum dots (Q-dots) have been developed that fluoresce with visible light under X-ray exposure. Q-dots thus may be said to allow detection of X-rays using visible light, though more properly the visible light fluorescence simply indicates that X-rays have been absorbed recently by the Q-dots. Because these Q-dots rapidly fluoresce in the presence of X-rays, and because the molecules of the Q-dots quickly recover to be able fluoresce again when additional X-rays strike the same area of Q-dots, Q-dots allow for the rapid characterization of X-rays using visible light.

Q-dots have been developed that fluoresce with visible light in response to exposure to more energetic gamma rays. Thus, all of the illustrative embodiments described herein with respect to X-rays may also be used with respect to the detection and characterization of gamma rays. Similarly, the illustrative embodiments may be used with respect to the detection and characterization of energetic electrons.

In an illustrative embodiment, Q-dots and Q-dot-based polymer nano-composites may be used as the indicators for X-ray scintillation and imaging applications. Q-dot indicators provide excellent X-ray luminescence, including high resolution, fast decay, non-afterglow, high stopping power, and a superior spectral match to a charged couple device detector. Thus, Q-dots may be a nanophosphor technique useful for X-ray indication and detection applications. Q-dots may be purchased from various companies, such as Evident Technologies, Inc. of Troy, New York. In a specific, non-limiting illustrative embodiment, Q-dots may be Cadmium Telluride (CdTe) Q-dots. Other Q-dots may be used.

Q-Dots and their nano-composites can be used in novel processes and arrangements that benefit from a visible indication of X-rays. The illustrative embodiments address these novel processes and arrangements.

FIG. 1 illustrates a side view of an X-ray backscatter indication and detection system 100, in accordance with an illustrative embodiment. X-ray backscatter indication and detection system 100 includes X-ray generator 102 that generates and directs X-rays 104 towards target area 106, which is part of target 108. X-rays 104 scatter from target area 106, creating backscattered X-rays. The backscattered X-rays are shown as arrows pointing away from target area 106.

Figure 2:
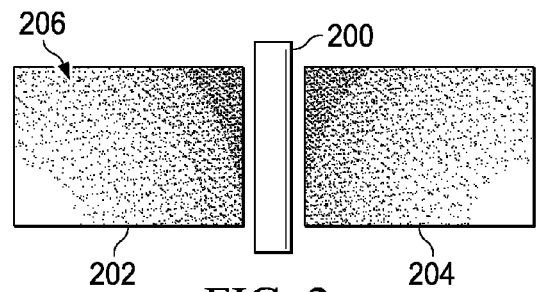
FIG. 2 illustrates an overhead view of X-ray backscatter indication and detection system shown in FIG. 1, in accordance with an illustrative embodiment.

Some of the backscattered X-rays strike one of panel 110 or panel 112. In an illustrative embodiment, panel 110 and panel 112 may both be traditional or conventional X-ray detectors, the surface of which has been treated with an X-ray fluorescent Q-dot solution. The panels 110 and 112 may be on the surface of objects having other shapes and functions, to which X-ray fluorescent Q-dots have been applied. Thus, the illustrative embodiments are not limited to flat rectangular objects, as shown in FIG. 1 and FIG. 2, and may have any desired shape, for example a curve or other shape. The two panels 110 and 112 are placed on either side of X-ray generator 102 specifically to intercept the backscattered X-rays. More or fewer X-ray detector panels may be present in different illustrative embodiments. In one illustrative embodiment, panel 110 and panel 112 are actually a single panel with a hole through which X-rays 104 from X-ray generator 102 are transmitted.

In the illustrative embodiment shown in FIG. 1, panel 110 includes layer 114 of an indicator solution, for example an X-ray fluorescent Q-dot solution, such as that described above. Panel 112 includes layer 116 of an X-ray fluorescent Q-dot solution, such as that described above. These X-ray fluorescent Q-dot solutions may be the same, but may also be different in concentration, atomic makeup, or otherwise different from each other, depending on a desired implementation of a backscatter X-ray monitor. In any case, the X-ray fluorescent Q-dot solutions fluoresce in the presence of backscattered X-rays.

Optionally, one or more detection devices, such as an image capturing device, for example camera 118 may be provided. Camera 118 may be configured to record the visible light fluorescence emitted by the X-ray fluorescent Q-dot solution when struck by X-rays. Camera 118 is optional, as in some cases a human operator may detect the visible light fluorescence. In other illustrative embodiments, a computer may be in communication with camera 118. An example of a computer may be data processing system 2000 shown in FIG. 20. In combination with servos or other mechanical devices connected to X-ray generator 102, the computer may be used to change operation of X-ray generator 102 in response to a particular characterization of the fluorescence. For example, if the fluorescence indicates that the flux of X-rays is undesirably high, then X-ray generator 102 may be commanded to generate fewer X-rays. Conversely, if the fluorescence indicates that the flux of X-rays is undesirably low, then X-ray generator 102 may be commanded to generate more X-rays. In another illustrative embodiment, if the fluorescence indicates that the flux of X-rays is hitting an incorrect location on target 108, then X-ray generator 102 may be commanded to change a direction in which it is pointing. These illustrative embodiments are exemplary only; other examples are possible. Thus, these illustrative embodiments do not necessarily limit the claimed inventions.

Likewise, panel 110 or panel 112 may be connected to mechanical actuators and may be moved in response to the fluorescence detected by camera 118. Still further, target 108 may be connected to mechanical actuators and may be moved in response to the fluorescence detected by camera 118. In another illustrative embodiment, all panels 110 and 112, target 108, and X-ray generator 102 may be controlled by a computer operating in response to fluorescence detected by camera 118.

FIG. 2 illustrates an overhead view of X-ray backscatter indication and detection system 100 shown in FIG. 1, in accordance with an illustrative embodiment. Thus, X-ray generator 200 corresponds to X-ray generator 102 of FIG. 1, panel 202 corresponds to panel 110 of FIG. 1, and panel 204 corresponds to panel 112 of FIG. 1. FIG. 2 shows the faces of panels 110 and 112 facing target 108 of FIG. 1. FIG. 2 shows that scattered X-rays cause an indicator such as X-ray fluorescent Q-Dots on the faces of the panels 202 and 204 to fluoresce and produce a visible light image of what the detectors in panels 110 and 112 are collecting.

Panels 202 and 204 may be termed X-ray backscatter detectors. Thus, surfaces of the X-ray backscatter detectors may be coated or sprayed with an X-ray fluorescent Q-dot solution. These detectors will show energy, extent, and shape of a scatter field in the backward or forward direction. For backscatter applications, using a fluorescent indicator such as X-ray fluorescent Q-dots, the surface of the detectors will visibly glow in the presence of X-rays to show a measurement of the distribution of the energy and flux of the X-rays that the detectors in the panels 202 and 204 are sensing. System parameters, including detector distance, size, source energy (which affects scatter) can all be optimized for best detection of the scatter from each part or structure under inspection. If the detector surfaces are not easily visible to the operator, a charged couple device (CCD), complimentary metal-oxide semiconductor (CMOS) camera, or some other detection device can be mounted on or near the panels 202 and 204, pointed at the panels, and hooked up to a monitor that the operator can observe. Likewise, the cameras may be connected to computers in order to modify operation of the X-ray generator, the panels, or the target, as described above. An example of such computers may be data processing system 2000 shown in FIG. 20. Note that in the situation where panel 110 and panel 112 contain other types of X-ray detectors, the X-ray fluorescent Q-dot solution provides a second means of verifying the characterization of X-rays measured using such other types of detectors, or for quickly verifying a desired position of the X-ray detectors with regard to the expected X-ray flux.

As can be seen in the general area of arrow 206, the intensity and/or the color of fluorescence may vary with the nature of the X-ray flux striking panel 202 or panel 204. The color or intensity of the fluorescence may indicate a lower or higher X-ray flux on a given portion of panel 202 or panel 204. In this manner, the X-ray flux may be visually characterized. In conjunction with a camera 118, a computer may also take the visible fluorescence as input and create a digital characterization and/or recording of the X-ray flux.

Figure 3:
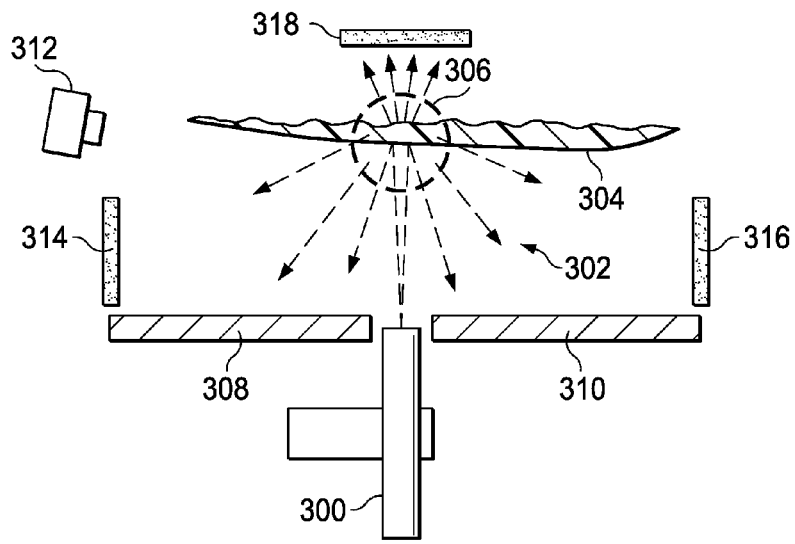
FIG. 3 illustrates another X-ray backscatter indication and detection system, in accordance with an illustrative embodiment.

FIG. 3 illustrates another X-ray backscatter indication and detection system, in accordance with an illustrative embodiment. The system shown in FIG. 3 is a variation of the systems shown in FIG. 1 and FIG. 2. Thus, relative to FIG. 1, X-ray generator 300 corresponds to X-ray generator 102, X-rays 302 correspond to X-rays 104, target area 306 corresponds to target area 106, target 304 corresponds to target 108, panel 308 corresponds to panel 110, panel 310 corresponds to panel 112 and camera 312 corresponds to camera 118.

However, in the variation shown in FIG. 3, the positions of the panels 308 and 310 have been modified. Panel 308 may be characterized as a first panel in front of but to a first side of X-ray generator 300 and panel 310 may be characterized as a second panel in front of but to a second side of X-ray generator 300, opposite the first side.

In an illustrative embodiment, the terms "first" and "second" may be interposed so that the other of panel 308 or panel 310 is considered the "first" panel. In an illustrative embodiment, both panels 308 and 310 may be a single panel with a hole or other aperture through which X-rays 302 may be transmitted.

In addition, panel 314 and panel 316 are provided at about right angles to panels 308 and 310, respectively. Panel 314 may be characterized as a third panel about perpendicular to the first panel 308 at a first far end of the first panel 308, relative to X-ray generator 300. Panel 316 may be characterized as a fourth panel about perpendicular to the second panel 310 at a second far end of the second panel 310, relative to X-ray generator 300. X-ray fluorescent Q-dots have been applied to the third panel 314 and the fourth panel 316 in order to visually characterize a portion of the X-rays scattered from target area 306.

In an illustrative embodiment, the third panel 314 and the fourth panel 316 are a single panel, such as in a circular panel or some other panel shape that wraps fully or partially around a perimeter of the first panel 308 and/or the second panel 310. In an illustrative embodiment, panels 308, 310, 314, and 316 are a single, continuous object shaped as shown. In an illustrative embodiment, the angles of any of the panels 308, 310, 314, and 316 shown may be changed with respect to each other. In an illustrative embodiment, X-ray fluorescent Q-dots may also be additionally placed on one or both of the first panel 308 or the second panel 310. Thus, the illustrative embodiments are not necessarily limited to the exact configuration shown in FIG. 3.

Optionally, panel 318 may be placed behind target area 306. Panel 318 may be characterized as a fifth panel behind target area 306 relative to X-ray generator 300. The fifth panel 318 may also be coated with X-ray fluorescent Q-dots. The fluorescence of X-ray fluorescent Q-dots on the fifth panel 318 may visually indicate the presence of X-rays scattered from target area 306 but not reflected back in a general direction towards X-ray generator 300.

The illustrative embodiment shown in FIG. 3 may be characterized as an X-ray scatter indicator. In this illustrative embodiment, the panels shown may be coated with an X-ray fluorescent Q-dot solution and placed at various locations around an X-ray backscatter test set-up. The panels may provide a measurement of the distribution of the energy and flux of the X-ray scatter in the forward or backward directions, on either side of the part under inspection; namely, target 304. The information provided by these scatter indicators may be useful for inspection procedure testing and optimization of system parameters. Camera 312 which is sensitive to visible light, can be used to capture the images of the fluorescence for display on a monitor and image data storage and analysis.

Figure 4:
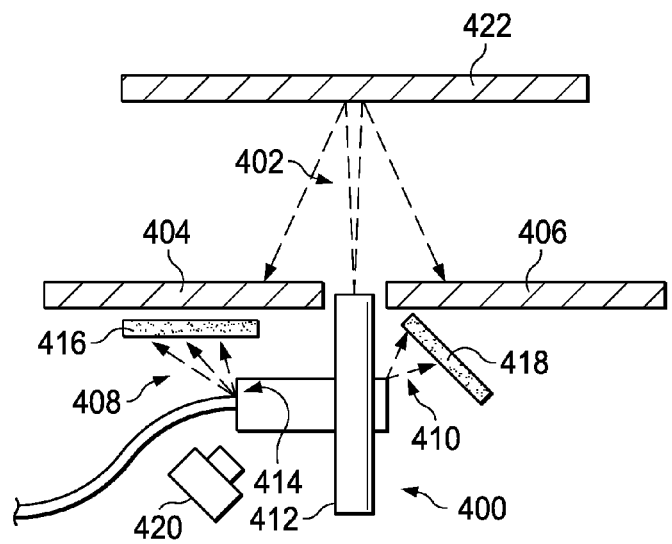
FIG. 4 illustrates an X-ray leak indication and detection system, in accordance with an illustrative embodiment.

FIG. 4 illustrates an X-ray leak indication and detection system, in accordance with an illustrative embodiment. The X-ray leak indication and detection system shown in FIG. 4 is a variation of the X-ray backscatter detection system shown in FIG. 1 through FIG. 3.

X-ray generator 400 may generate additional X-rays that are not intended for emission towards target 422. Such X-rays may be characterized as "leaked" X-rays. As shown in FIG. 4, X-rays 408 and X-rays 410 are leaked X-rays. Leaked X-rays typically may be emitted from collimator 412 of X-ray generator 400, as shown by X-rays 408. Leaked X-rays also typically may be emitted from portions of the housing of X-ray generator 400 from which cables emerge, such as generally at area 414, as shown by X-rays 408. Areas of the housing of X-ray generator 400 from which cables emerge typically have less shielding, meaning that in some cases leaked X-rays may be emitted from these areas.

A useful visible indicator for detecting leaked X-rays may take the form of objects such as panels coated with indicators such as X-ray fluorescent Q-dots. Thus, panel 416 and panel 418 are provided, each coated with X-ray fluorescent Q-dots. Panel 416 may be disposed and angled in order to efficiently detect leaked X-rays 408. Similarly, panel 418 may be disposed and angled in order to efficiently detect leaked X-rays 410.

In an illustrative embodiment, panel 416 and panel 418 may be disposed on either side of X-ray generator 400, at an angle with respect to each other and a direction of travel of emitted X-rays 402. This angle may be any desired angle relative to each other so that the detection or indication of any leaked X-ray flux is maximized within the sensor area. In other words, the angles may be selected based on an expected direction of travel of leaked X-rays. This angle, alternatively, may be made with reference to some other object.

To ensure that only leaked X-rays are detected, one or more shields for intercepting X-rays backscattered from a target may be present. For example, shield 404 and shield 406 prevent the transmission of X-rays backscattered from target 422, which may be target 108 of FIG. 1. These shields may also serve a double purpose as backscattered x-ray detectors or panels coated with X-ray fluorescent Q-dots in order to detect backscattered X-rays. Thus, for example, shield 404 may correspond to panel 110 of FIG. 1 and shield 406 may correspond to panel 112 of FIG. 1. In any case, shield 404 and shield 406 prevent X-rays backscattered from target 422 from being confused with leaked X-rays that may be emitted from X-ray generator 400, for example.

Variations to the illustrative embodiments described above are possible. In an example, panel 416 and panel 418 may have any desired shape. In another example more or fewer panels may be present. In another example, shield 404 and shield 406 may be a single unitary shield, or may be multiple additional shields. Shield 404 and shield 406 may have any desired shape. Any of panel 416, panel 418, shield 404, and shield 406 may also serve a double function as an X-ray detector material, an X-ray film, or X-ray sensitive camera. Either or both of panel 416 and panel 418 may serve a double function as shielding intended to block leaked X-rays from leaving the area of the X-ray generating equipment.

Optionally, camera 420 may be provided to optically monitor fluorescence from panel 416 and/or panel 418. A computer, such as data processing system 2000 of FIG. 20, may be connected to camera 420. The computer may receive optical data from the camera, and then store or analyze the pattern of fluorescent light emitted from panel 416 and or panel 418. In an illustrative embodiment, operation of X-ray generator 400 may be controlled based on such an analysis. For example, if a flux of leaked X-rays exceeds a threshold value, then X-ray generator 400 may be shut down or be commanded to generate fewer emission X-rays 402. Alternatively, adjustments may be made, either manually or automatically, to any part of X-ray generator 400 in order to minimize detected leaks of X-rays, based on the analysis of the fluorescence from panel 416 and/or panel 418.

Thus, FIG. 4 shows an example of one or more X-ray Leak detection screens. In one illustrative embodiment, X-rays fluorescent Q-Dots may be mixed into a carrier and sprayed onto a screen, such as panel 416 and/or panel 418. The screen may be placed adjacent to x-ray systems, such as X-ray generator 400, but also including other x-ray sources, x-ray backscatter systems, portable digital x-ray systems, and the like. The screen may be used to check for or to monitor leaks in the X-rays system. Leaks of X-rays typically may occur at the source attachment, where the cables exit the source, in the collimator, and other locations on X-ray generator 400. Monitoring of fluorescence from the screen can be performed using operator observance at a distance. Alternatively, a visible light camera, such as a CCD camera or CMOS camera, can be mounted on or near the screen and aimed at the cover, so that the camera can capture Q-Dot fluorescence images for display on a monitor or for analysis by a computer.

As indicated above, the arrangements shown in FIG. 4 may be varied. Accordingly, the illustrative embodiments shown in FIG. 4 do not necessarily limit the claimed inventions.

Figure 5:
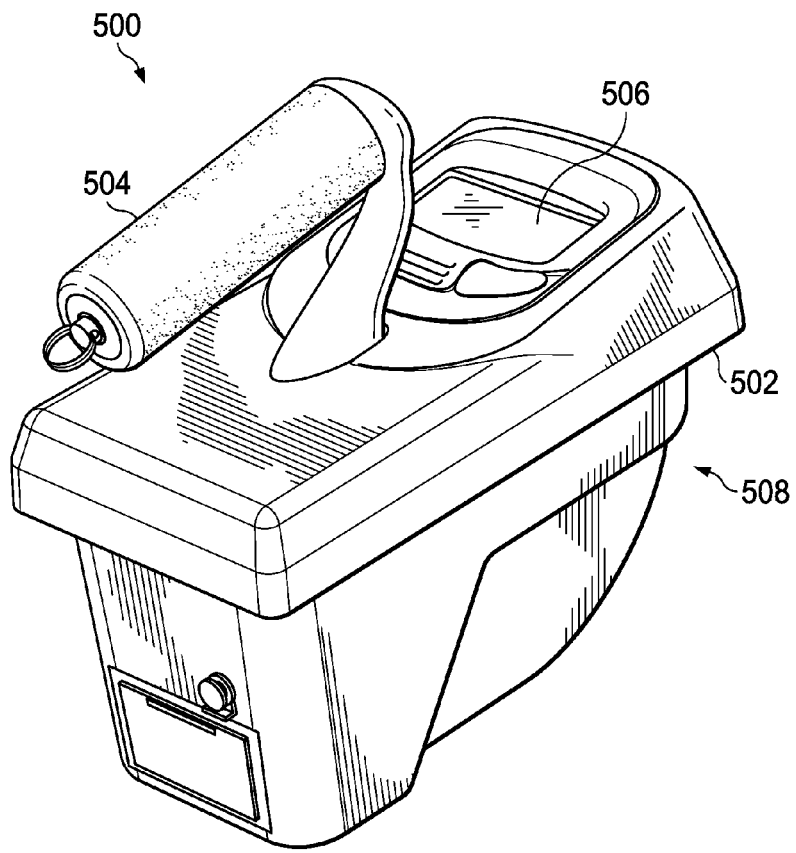
FIG. 5 illustrates an X-ray monitor, in accordance with an illustrative embodiment.
Figure 6:
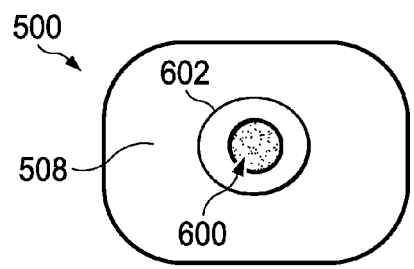
FIG. 6 illustrates a front-on view of the X-ray monitor of FIG. 5, in accordance with an illustrative embodiment.

FIG. 5 illustrates an X-ray monitor, in accordance with an illustrative embodiment. FIG. 6 illustrates a front-on view of the X-ray monitor of FIG. 5, in accordance with an illustrative embodiment. FIG. 5 and FIG. 6 refer to the same X-ray monitor; thus, FIG. 5 and FIG. 6 use common reference numerals. In an illustrative embodiment, X-ray monitor 500 may be used in place of any of the X-ray fluorescent Q-dot coated panels shown in FIG. 1 through FIG. 4. In an illustrative embodiment, X-ray monitor 500 may be an ion chamber X-ray monitor, though X-ray monitor 500 could be an X-ray survey meter or any other X-ray detector.

Whatever form X-ray monitor 500 takes, X-ray monitor 500 includes housing 502 in which equipment for detecting and measuring X-rays is located. For portability, X-ray monitor 500 may be provided with handle 504. Screen 506 may display readings of any detected X-ray flux. With the illustrative embodiment shown in FIG. 5, X-ray monitor 500 is most sensitive when the X-ray flux is directed at front 508 of X-ray monitor 500.

Turning now to FIG. 6, sensor area 600 may be an area of X-ray monitor 500 which is most sensitive to an incoming X-ray flux. X-ray fluorescent Q-dots 602 may be placed on or around sensor area 600 to form a spot indicator. Thus, X-ray fluorescent Q-dots 602 may extend past and surround sensor area 600, and/or cover part or all of sensor area 600.

X-ray fluorescent Q-dots 602 may fluoresce in the presence of an X-ray flux. If the source of X-ray flux is in a relatively tight beam, X-ray fluorescent Q-dots 602 may be used to help guide a position or angle of X-ray monitor 500 so that the direction of X-ray flux is maximized within sensor area 600.

For example, if fluorescence by X-ray fluorescent Q-dots 602 increases as X-ray monitor 500 moves, then it may be assumed that more X-rays are entering sensor area 600. Conversely, if fluorescence by X-ray fluorescent Q-dots 602 decreases as X-ray monitor 500 moves, then it may be assumed that fewer X-rays are entering sensor area 600. X-ray monitor 500 may be moved back and forth or otherwise angled, using the visible fluorescence of X-ray fluorescent Q-dots 602 as a guide for moving X-ray monitor 500, until a maximum flux of X-rays is entering sensor area 600.

If X-ray monitor 500 is connected to a computer and a movement mechanism, and the fluorescence of X-ray fluorescent Q-dots 602 monitored with one or more visible light cameras, then X-ray monitor 500 may be automatically adjusted to maximize the amount of X-rays entering sensor area 600. For example, the camera may monitor the fluorescence from X-ray fluorescent Q-dots 602 and transmit corresponding data to the computer. In turn, the computer can command the movement mechanism to move X-ray monitor 500 such that the amount of visible fluorescence emitted from X-ray fluorescent Q-dots 602 is maximized.

Figure 7:
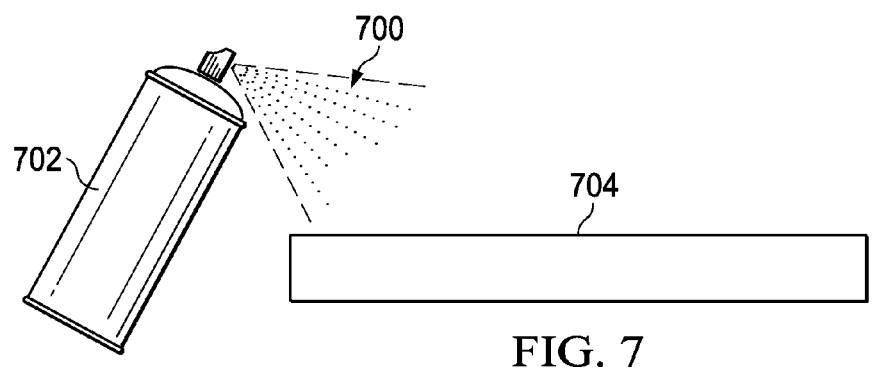
FIG. 7 illustrates a technique for applying an X-ray fluorescent Q-dot solution, in accordance with an illustrative embodiment.

FIG. 7 illustrates a technique for applying an X-ray fluorescent Q-dot solution, in accordance with an illustrative embodiment. This technique may be used with respect to applying X-ray fluorescent Q-dots to any of the panels or devices shown in FIG. 1 through FIG. 6.

X-ray fluorescent Q-dots 700 may be applied to the surface of panels by spraying, painting, dipping or other means. For example, X-ray fluorescent Q-dots 700 may be placed in a solution and placed in aerosol device 702. Aerosol device 702 may then be used to spray or coat the surface of object 704. Object 704 may be any of the panels described with respect to FIG. 1 through FIG. 4, or an X-ray monitor, such as X-ray monitor 500 of FIGS. 5 and 6. Aerosol device 702 may be replaced by a hand-pumped spraying device, or any other suitable device for applying a solution to an object.

Thus, X-ray fluorescent Q-dot mixtures can be created to indicate by color impinging x-rays. These solutions can be mixed into coatings or paints to be sprayed or otherwise applied onto various structures as an x-ray witness.

Thus, FIG. 7 provides for an inspection X-ray sensitive indicator spray. X-ray fluorescent Q-dots may be mixed in a liquid carrier that is sprayed using aerosol or compressed air onto indicator structures to show X-ray impingement visibly in an x-ray vault. The surface can be an x-ray table, or back wall onto which x-rays are emitted from a source. Object 704 may be a flat panel placed behind or beside an X-ray detector or film to show visibly where the x-rays are. The spray can be removable or permanent.

Figure 8:
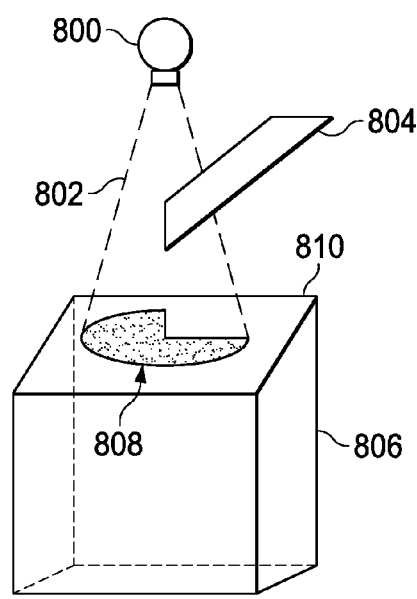
FIG. 8 illustrates a technique for characterizing X-rays striking a detector, in accordance with an illustrative embodiment.

FIG. 8 illustrates a technique for characterizing X-rays striking a detector, in accordance with an illustrative embodiment. FIG. 8 is a variation of the systems and methods shown in FIG. 1 through FIG. 6 for indicating and detecting X-rays.

X-ray generator 800 generates X-rays 802, which are directed at least in part at target 804. Target 804 may be an object of study or part under inspection using X-rays 802. Some of X-rays 802 may be blocked or transmitted through target 804. The pattern of X-rays reaching detector 806 may be shown visibly using X-ray fluorescent Q-dots 808 disposed on detector 806.

Thus, X-ray fluorescent Q-dots may be mixed in a liquid carrier that is sprayed or painted onto cover 810 in front of detector 806. The X-ray fluorescent Q-dots will fluoresce when hit by X-rays 802 allowing an operator to readily visualize when and where the x-rays 802 are impinging on detector 806. This visible information can be used to rapidly inform the operator when x-rays 802 are present, for example, without using detection equipment.

This visible information may also be used for pre-inspection imaging of target 804 before detector 806 is used. For example, this visible information can show a cross-section and size of X-rays 802 at a distance from X-ray generator 800 prior to and/or after setting up target 804 for inspection. This visible information can also show how x-rays 802 are attenuating through target 804.

Figure 9:
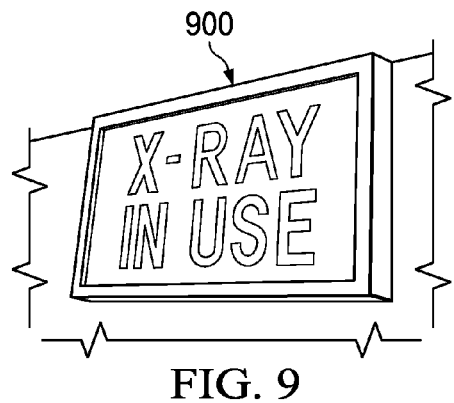
FIG. 9 illustrates a pattern of X-ray fluorescent Q-dots on a surface, in accordance with an illustrative embodiment.
Figure 10:
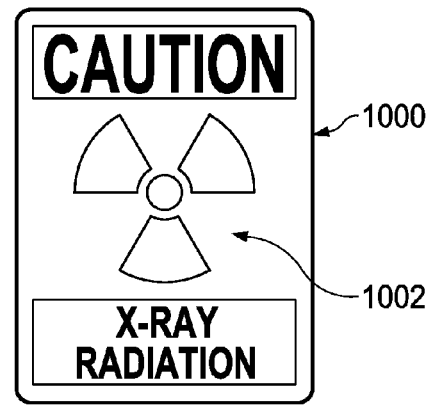
FIG. 10 illustrates another pattern of X-ray fluorescent Q-dots on a surface, in accordance with an illustrative embodiment.

FIG. 9 illustrates a pattern of X-ray fluorescent Q-dots on a surface, in accordance with an illustrative embodiment. FIG. 10 illustrates another pattern of X-ray fluorescent Q-dots on a surface, in accordance with an illustrative embodiment. Thus, FIGS. 9 and 10 each represent exemplary patterns of X-ray fluorescent Q-dots that may be placed on an object. Many other patterns are possible. These patterns could be placed on any of the panels or objects shown with respect to FIG. 1 through FIG. 8.

FIG. 9 shows sign 900. In an illustrative embodiment, some or all of the letters in the words "X-RAY IN USE" on sign 900 may be formed using X-ray fluorescent Q-dots. Thus, when X-rays strike sign 900, part or all of these letters may glow in a visible light, indicating to a user that X-rays are striking sign 900. The user may then take any appropriate action knowing that X-rays are in the vicinity.

FIG. 10 shows sign 1000. Like sign 900, X-ray fluorescent Q-dots may be used in a pattern to indicate the presence of X-rays. However, for sign 1000, X-ray fluorescent Q-dots are arranged in the shape of radiation warning symbol 1002. Thus, when X-rays strike radiation warning symbol 1002, the symbol may be detected as a "glow" by an observer without the aid of detection equipment to indicate the presence of X-rays. In an illustrative embodiment, the words surrounding radiation warning symbol 1002 may also be treated with X-ray fluorescent Q-dots and glow in the presence of X-rays. In an illustrative embodiment, only the words surrounding radiation warning symbol 1002 are treated with X-ray fluorescent Q-dots and glow in the presence of X-rays. Many other variations are possible.

Thus, FIG. 9 and FIG. 10 represent non-powered indicators for the presence of X-rays. Letters or symbols may be made using X-ray fluorescent Q-dots that light up in the presence of X-rays. These sign or safety witnesses, or indicators, may be set at an edge of a generated beam so that the sign lights up when the generated beam is on. An operator may see the sign right away when approaching the inspection set-up.

In a variant illustrative embodiment, a camera can be used to capture the images of the signs for display on one or more monitors at other locations. Thus, the presence of X-rays may be visibly monitored from remote locations.

Figure 11:
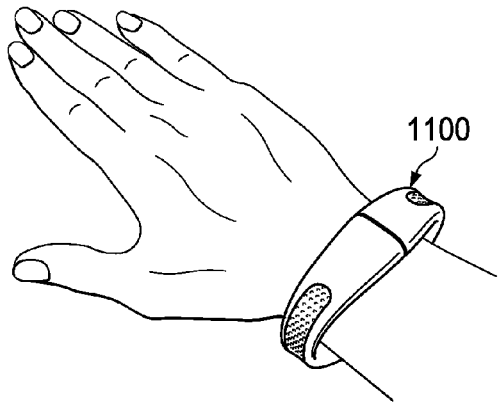
FIG. 11 illustrates an article of apparel treated with X-ray fluorescent Q-dots, in accordance with an illustrative embodiment.
Figure 12:
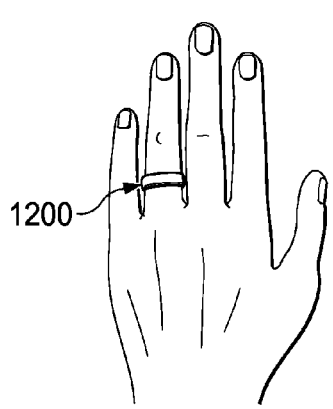
FIG. 12 illustrates another article of apparel treated with X-ray fluorescent Q-dots, in accordance with an illustrative embodiment.
Figure 13:
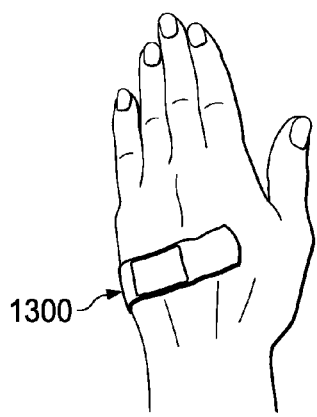
FIG. 13 illustrates another article of apparel treated with X-ray fluorescent Q-dots, in accordance with an illustrative embodiment.

FIG. 11 illustrates an article of apparel treated with X-ray fluorescent Q-dots, in accordance with an illustrative embodiment. FIG. 12 illustrates another article of apparel treated with X-ray fluorescent Q-dots, in accordance with an illustrative embodiment. FIG. 13 illustrates another article of apparel treated with X-ray fluorescent Q-dots, in accordance with an illustrative embodiment. Thus, FIG. 11 through FIG. 13 represent different illustrative embodiments of X-ray fluorescent Q-dot treated articles of apparel for visibly indicating the presence of X-rays.

FIG. 11 shows wrist band 1100, which has been treated with X-ray fluorescent Q-dots. FIG. 12 shows ring 1200, which has been treated with X-ray fluorescent Q-dots. FIG. 13 shows adhesive strip 1300, which has been treated with X-ray fluorescent Q-dots. Each of these articles of apparel may be worn on a part of a human body in order to visibly indicate the presence of X-rays.

In an illustrative embodiment, the concentration or density of X-ray fluorescent Q-dots may be set so that the fluorescence light emitted by the X-ray fluorescent Q-dots is difficult to detect when only natural background X-rays are present. Thus, these articles of apparel fluoresce with a bright intensity only when a higher than background intensity of X-rays is present, signaling to an observer that a threshold amount of X-rays is being emitted.

In other illustrative embodiments, the indicators may be applied to the surface of other portable objects. For example, adhesive strip 1300 may be a tape that may be applied to any convenient surface in an X-ray vault or other area where an X-ray flux is to be monitored. In another example, wristband 1100 may be wrapped around a machine or mobile robot which is expected to encounter an X-ray flux. In another example, the X-ray fluorescent Q-dot treated article of apparel may be a badge, a shirt, a hat, or any other object. Thus, the illustrative embodiments are not necessarily limited to the objects shown in FIG. 11 through FIG. 13.

The illustrative embodiments shown in FIG. 11 through FIG. 13 provide a means for rapid visible indication of radiation exposure. The indicator may be provided to people working around X-ray radiation in medical, industrial, and commercial areas.

Figure 14:
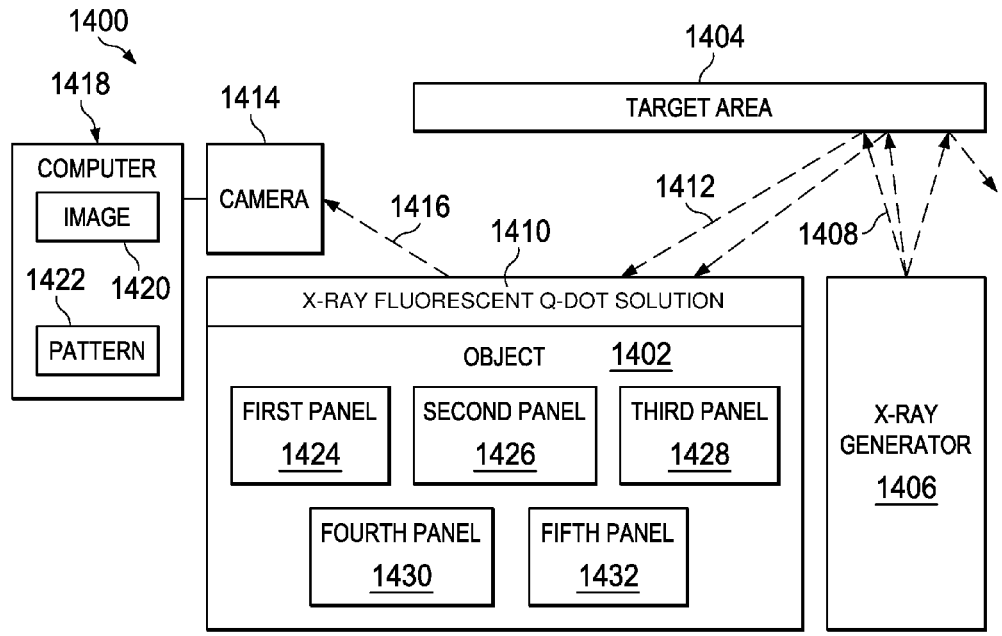
FIG. 14 is an X-ray backscatter indication and detector system, in accordance with an illustrative embodiment.

FIG. 14 is an X-ray backscatter indication and detector system, in accordance with an illustrative embodiment. Backscatter indication and detection system 1400 may be a variation of the embodiments depicted in FIG. 1 through FIG. 3.

Backscatter indication and detection system 1400 includes object 1402 disposed with respect to target area 1404 targeted by X-ray generator 1406, such that X-rays 1408 from X-ray generator 1406 that backscatter from target area 1404 can strike object 1402. The surface of object 1402 is coated with X-ray fluorescent Q-dot solution 1410 that is configured to fluoresce with a visible light when X-rays 1412 strike X-ray fluorescent Q-dot solution 1410.

This illustrative embodiment may be varied. Thus, for example, backscatter indication and detection system 1400 may also include camera 1414 operatively disposed with respect to object 1402 such that camera 1414 can detect visible light 1416 resulting from fluorescence of X-ray fluorescent Q-dot solution 1410.

In an illustrative embodiment, backscatter indication and detection system 1400 may also include computer 1418 in communication with camera 1414. Computer 1418 may be configured to store image 1420 of visible light 1416 and to perform an analysis of image 1420. An example of computer 1418 may be data processing system 2000 shown in FIG. 20.

In an illustrative embodiment, backscatter indication and detection system 1400 may include X-ray generator 1406, which may be in communication with computer 1418. Computer 1418 may be further configured to modify operation of X-ray generator 1406 based on the analysis of image 1420 of visible light 1416 taken by camera 1414.

In an illustrative embodiment, computer 1418 may be further configured to analyze pattern 1422 of backscattered X-rays 1412 based on visible light 1416 and determine whether pattern 1422 matches an expected pattern of backscattered X-rays. In being configured to modify operation of X-ray generator 1406, computer 1418 is configured to modify operation of X-ray generator 1406 based on pattern 1422.

In an illustrative embodiment, backscatter indication and detection system 1400 may include one or more of first panel 1424, second panel 1426, third panel 1428, fourth panel 1430, and fifth panel 1432. First panel 1424 may be in front of but to a first side of X-ray generator 1406. Second panel 1426 may be in front of but to a second side of X-ray generator 1406, opposite the first side. Third panel 1428 may be about perpendicular to first panel 1424 at a first far end of first panel 1424, relative to X-ray generator 1406. Fourth panel 1430 may be about perpendicular to second panel 1426 at a second far end of second panel 1426, relative to X-ray generator 1406. Fifth panel 1432 may be behind target area 1404 relative to X-ray generator 1406.

In an illustrative embodiment, X-ray fluorescent Q-dot solution 1410 may be disposed on one or more of panels 1424 through 1432. Thus, X-ray fluorescent Q-dot solution 1410 may be on panels selected from the group consisting of: 1) first panel 1424 and second panel 1426; 2) first panel 1424, second panel 1426, and fifth panel 1432; and 3) all of first panel 1424, second panel 1426, third panel 1428, fourth panel 1430, and fifth panel 1432.

Other variations of backscatter indication and detection system 1400 are possible. For example, any of first panel 1424, second panel 1426, third panel 1428, fourth panel 1430, and fifth panel 1432 may be characterized as "objects" as their shapes are not limited to panels, as already described with respect to FIG. 14 and FIG. 15 and as claimed below. Likewise, object 1402 may be characterized as any or a combination of first panel 1424 through fifth panel 1432. In an illustrative embodiment, object 1402 may be characterized as a "first object", such as already described with respect to FIG. 15, below. Thus, the illustrative embodiments of FIG. 14 do not necessarily limit the claimed inventions.

Figure 15:
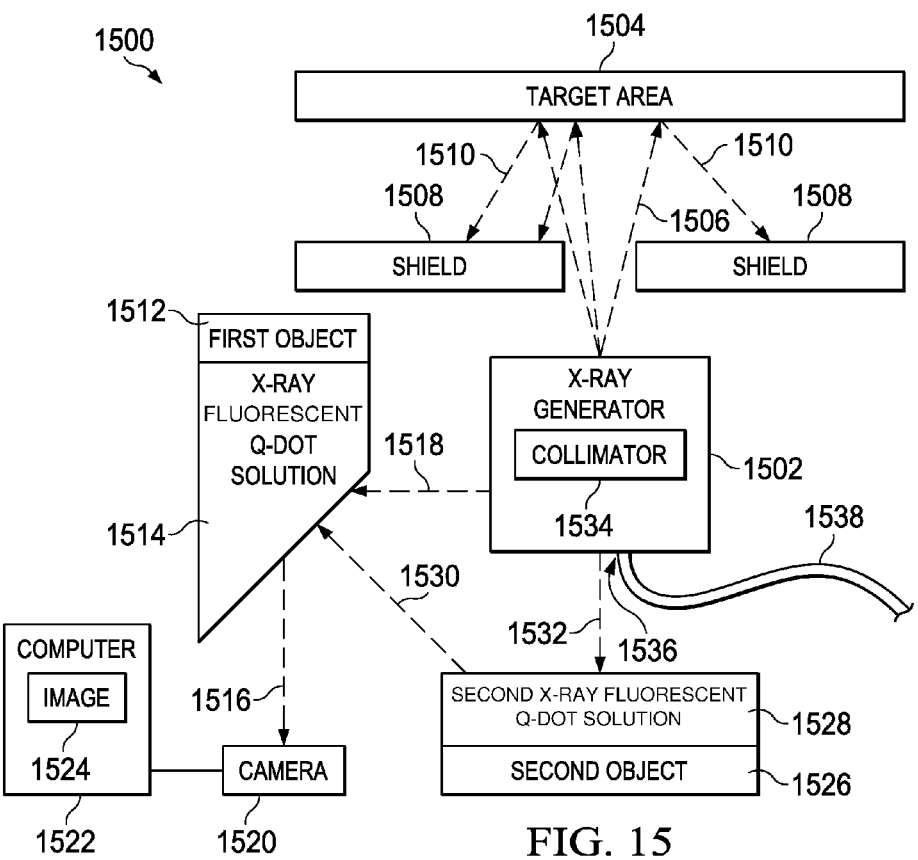
FIG. 15 is an X-ray leak detector, in accordance with an illustrative embodiment.

FIG. 15 is an X-ray leak detector, in accordance with an illustrative embodiment. X-ray leak detector 1500 may be a variation of the X-ray leak detector shown in FIG. 4.

In an illustrative embodiment, X-ray leak detector 1500 includes X-ray generator 1502 and target area 1504 disposed such that X-rays 1506 generated by X-ray generator 1502 strike target area 1504. X-ray leak detector 1500 also may include shield 1508 disposed in front of X-ray generator 1502. Shield 1508 may be configured to block X-rays 1510 backscattered from target area 1504. Shield 1508 may be one or more panels.

X-ray leak detector 1500 may also include first object 1512 disposed behind shield 1508 relative to target area 1504. X-ray fluorescent Q-dot solution 1514 may be disposed on first panel first object 1512. X-ray fluorescent Q-dot solution 1514 may be configured to fluoresce with visible light 1516 when X-rays 1518 strike X-ray fluorescent Q-dot solution 1514.

In an illustrative embodiment, X-ray leak detector 1500 may also include camera 1520 operatively disposed with respect to first object 1512 such that camera 1520 can detect visible light 1516 resulting from fluorescence of X-ray fluorescent Q-dot solution 1514. In this case, X-ray leak detector 1500 may further include computer 1522 in communication with camera 1520. Computer 1522 may be configured to store image 1524 of visible light 1516 and to perform an analysis of visible light 1516. An example of computer 1522 may be data processing system 2000 shown in FIG. 20.

In an illustrative embodiment, X-ray leak detector 1500 may include second object 1526 disposed behind shield 1508 relative to target area 1504. Second object 1526 may be further disposed opposite first object 1512 relative to X-ray generator 1502. In this case, second X-ray fluorescent Q-dot solution 1528 may be disposed on second object 1526. Second X-ray fluorescent Q-dot solution 1528 may be configured to fluoresce with visible light 1530 when X-rays 1532 strike second X-ray fluorescent Q-dot solution 1528.

In an illustrative embodiment, first object 1512 and second object 1526 may be disposed at an angle with respect to each other, the angle being relative to a direction of X-rays 1506 intended to be emitted by X-ray generator 1502. In another illustrative embodiment, first object 1512 may be disposed to receive X-rays 1518 (which may be characterized as first X-rays) leaked from collimator 1534. X-ray generator 1502 and second object 1526 may be disposed to receive X-rays 1532 (which may be characterized as second X-ray) leaked from location 1536 where cable 1538 exits from X-ray generator 1502. In an illustrative embodiment, either or both of first object 1512 or second object 1526 may be characterized as a first panel and a second panel, respectively.

Figure 16:
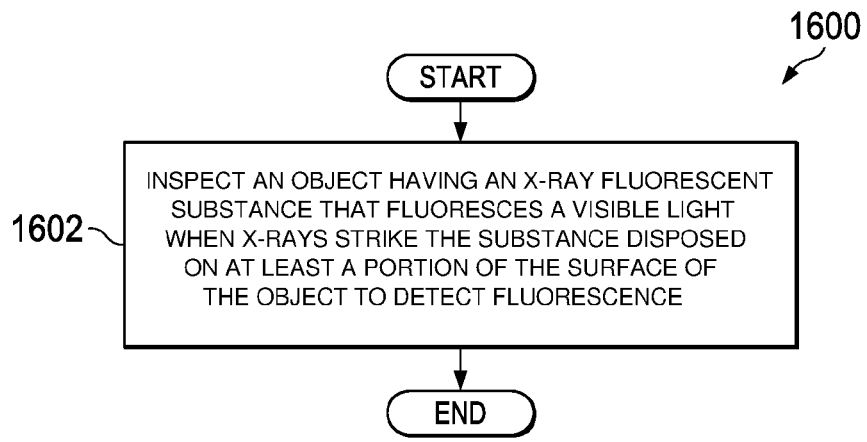
FIG. 16 is a flowchart of a method for inspecting an article, in accordance with an illustrative embodiment.

FIG. 16 is a flowchart of a method for inspecting an article, in accordance with an illustrative embodiment. Method 1600 may be implemented using any of the X-ray fluorescent Q-dot treated objects shown in FIG. 11 through FIG. 13.

Method 1600 may begin by inspecting an object having an X-ray fluorescent substance that fluoresces a visible light when X-rays strike the substance disposed on at least a portion of the surface of the object to detect fluorescence (operation 1602). The process may terminate thereafter.

This method may be varied. For example, the article may be an article of apparel selected from the group consisting of: a ring, a bracelet, a cloth, and a badge. The article may be any object, whether worn by individuals or attached to machines.

Figure 17:
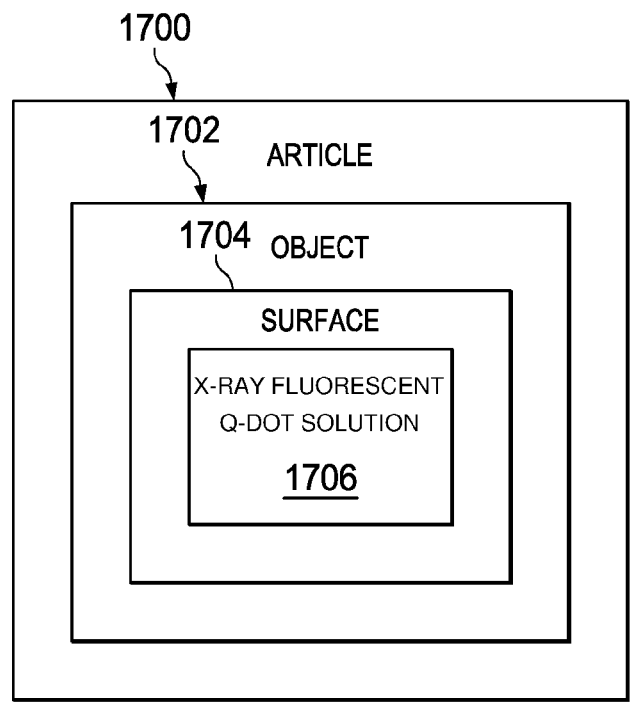
FIG. 17 is an article including a pattern of an X-ray fluorescent Q-dot solution on the surface of an object, in accordance with an illustrative embodiment.

FIG. 17 is an article including a pattern of an X-ray fluorescent Q-dot solution on the surface of an object, in accordance with an illustrative embodiment. Article 1700 may be a variation of any of the signs shown in FIG. 9 and FIG. 10.

Article 1700 may include object 1702 including surface 1704. X-ray fluorescent Q-dot solution 1706 may be disposed on surface 1704. X-ray fluorescent Q-dot solution 1706 may be configured to fluoresce with a visible light when X-rays strike X-ray fluorescent Q-dot solution 1706. X-ray fluorescent Q-dot solution 1706 may be placed on surface 1704 in a pattern selected from the group consisting of: a word, alphanumeric characters, and an image. This pattern may take any shape, letter, number, or symbol.

Figure 18:
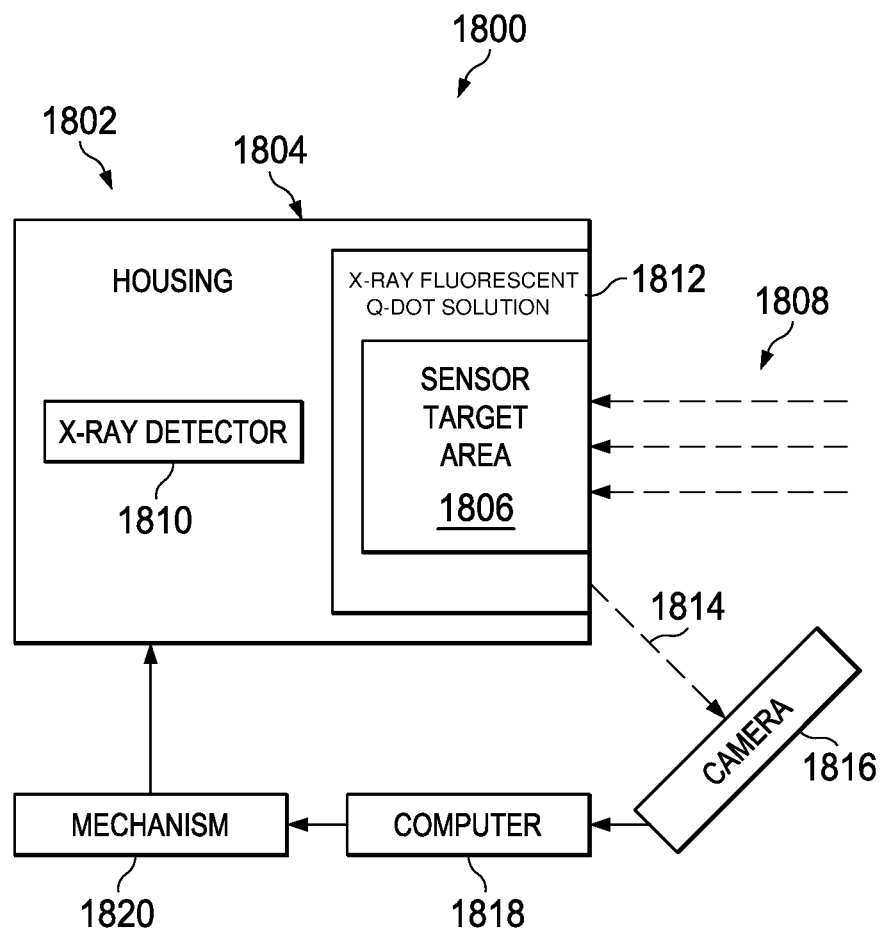
FIG. 18 is an X-ray monitor, in accordance with an illustrative embodiment.

FIG. 18 is an X-ray monitor, in accordance with an illustrative embodiment. X-ray monitor 1800 may be an example of X-ray monitor 500 of FIG. 5 and FIG. 6.

X-ray monitor 1800 may include X-ray measuring tool 1802. X-ray measuring tool 1802 may include housing 1804. X-ray measuring tool 1802 may include sensor target area 1806 on housing 1804 and configured to receive X-ray flux 1808. X-ray measuring tool 1802 may include X-ray detector 1810 disposed inside housing 1804 and configured to measure X-ray flux 1808. X-ray measuring tool 1802 may also include X-ray fluorescent Q-dot solution 1812 disposed on sensor target area 1806. X-ray fluorescent Q-dot solution 1812 may be configured to fluoresce with visible light 1814 when X-rays, such as X-ray flux 1808, strike X-ray fluorescent Q-dot solution 1812.

This illustrative embodiment may be varied. For example, X-ray fluorescent Q-dot solution 1812 may further extend past and surround sensor target area 1806. However, X-ray fluorescent Q-dot solution 1812 may take less or more area.

In an additional illustrative embodiment, Camera 1816 may be disposed to monitor visible light 1814. Computer 1818 may be connected to camera 1816. Computer 1818 may be configured to determine whether an expected amount of X-ray flux 1808 is entering sensor target area 1806 based on a characterization of visible light 1814. An example of computer 1818 may be data processing system 2000 shown in FIG. 20.

In yet another illustrative embodiment, mechanism 1820 may be connected to computer 1818. Mechanism 1820 may be configured to adjust an orientation of X-ray measuring tool 1802. Computer 1818 may be further configured to command mechanism 1820 to adjust the orientation based on the characterization such that a desired amount of X-ray flux 1808 is entering sensor target area 1806.

Other variations are also possible. Thus, the illustrative embodiments shown with respect to FIG. 18 do not necessarily limit the claimed inventions.

Figure 19:
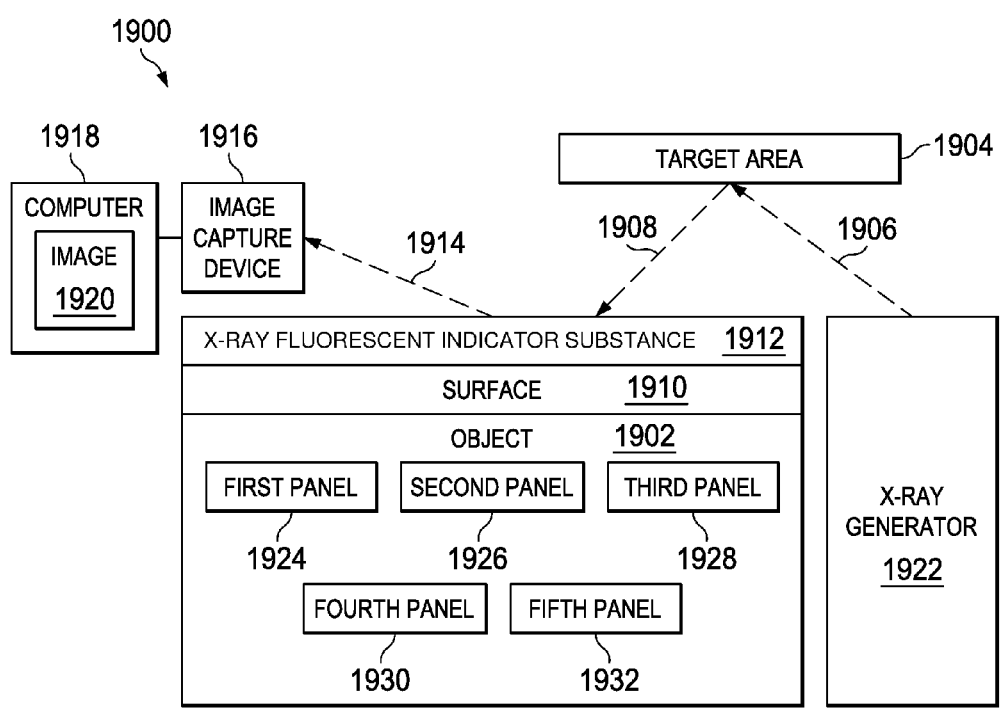
FIG. 19 is an X-ray backscatter indication and detection system, in accordance with an illustrative embodiment.

FIG. 19 is an X-ray backscatter indication and detection system 1900, in accordance with an illustrative embodiment. The X-ray backscatter indication and detection system 1900 may be a variation of the embodiments depicted in FIG. 1 through FIG. 3, as well as a variation of backscatter indication and detection system 1400 of FIG. 14.

X-ray backscatter indication and detection system 1900 includes object 1902 disposed with respect to target area 1904 targeted by X-rays 1906, such that backscattered X-rays 1908 that backscatter from target area 1904 strike surface 1910 of object 1902. Surface 1910 of object 1902 includes X-ray fluorescent indicator substance 1912 that fluoresces with visible light 1914 when contacted by backscattered X-rays 1908.

X-ray backscatter indication and detection system 1900 may be varied. For example, in an illustrative embodiment, X-ray fluorescent indicator substance 1912 that fluoresces may be a Q-dot solution. In another illustrative embodiment, an additional X-ray fluorescent indicator substance may be provided. The additional X-ray fluorescent indicator substance may be placed on, next to, or below X-ray fluorescent indicator substance 1912. The additional X-ray fluorescent indicator substance may cover part of surface 1910 while X-ray fluorescent indicator substance 1912 covers another part of surface 1910.

In another illustrative embodiment, X-ray backscatter indication and detection system 1900 may further include image capture device 1916 operatively disposed with respect to object 1902 to detect visible light 1914 resulting from fluorescence of X-ray fluorescent indicator substance 1912. In still another illustrative embodiment, X-ray backscatter indication and detection system 1900 may also include computer 1918 in communication with image capture device 1916, which stores image 1920 of visible light 1914 and performs an analysis of image 1920. An example of computer 1918 may be data processing system 2000 shown in FIG. 20.

In yet another illustrative embodiment, X-ray backscatter indication and detection system 1900 may include X-ray generator 1922. However, X-ray generator 1922 is not necessary to the operation of the illustrative embodiments shown in FIG. 19. X-ray generator 1922, may be in communication with computer 1918 in communication with image capture device 1916. In this case, computer 1918 may modify operation of X-ray generator 1922 based on the analysis of image 1920 of visible light 1914 taken by image capture device 1916.

In still another illustrative embodiment, object 1902 may take a variety of forms. For example, object 1902 may be first panel 1924 in front of but to a first side of X-ray generator 1922. In addition or in place of first panel 1924, object 1902 may also include second panel 1926 in front of but to a second side of X-ray generator 1922, opposite the first side. In addition or in place of first panel 1924 and/or second panel 1926, object 1902 may also include third panel 1928 about perpendicular to first panel 1924 at a first far end of first panel 1924, relative to X-ray generator 1922. In addition or in place of first panel 1924, second panel 1926 and/or third panel 1928, object 1902 may also include fourth panel 1930 about perpendicular to second panel 1926 at a second far end of second panel 1926, relative to X-ray generator 1922. In addition or in place of first panel 1924, second panel 1926, third panel 1928, and/or fourth panel 1930, object 1902 may also include fifth panel 1932 behind target area 1904 relative to X-ray generator 1922.

Additional variations are possible. Thus, the illustrative embodiments are not necessarily limited to the illustrative embodiments shown in FIG. 19. Accordingly, the illustrative embodiments shown in FIG. 19 do not necessarily limit the claimed inventions.

Figure 20:
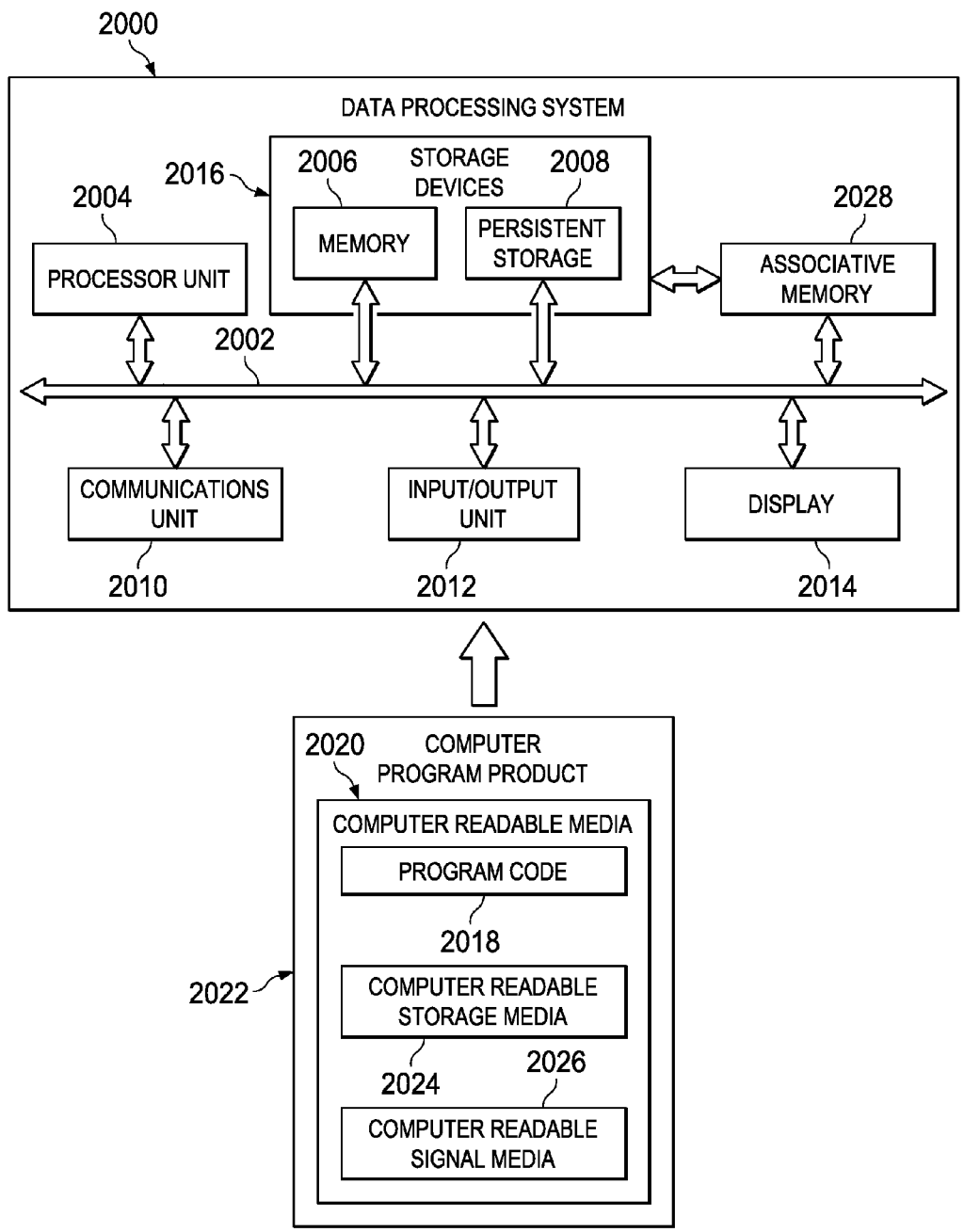
FIG. 20 is an illustration of a data processing system, in accordance with an illustrative embodiment.

Turning now to FIG. 20, an illustration of a data processing system is depicted in accordance with an illustrative embodiment. Data processing system 2000 in FIG. 20 is an example of a data processing system that may be used to implement the illustrative embodiments, such as method 1600 of FIG. 16, the characterization of fluorescing light from FIG. 1 through FIG. 13, or any other module or system or process disclosed herein. In this illustrative example, data processing system 2000 includes communications fabric 2002, which provides communications between processor unit 2004, memory 2006, persistent storage 2008, communications unit 2010, input/output (I/O) unit 2012, and display 2014.

Processor unit 2004 serves to execute instructions for software that may be loaded into memory 2006. Processor unit 2004 may be a number of processors, a multi-processor core, or some other type of processor, depending on the particular implementation. A number, as used herein with reference to an item, means one or more items. Further, processor unit 2004 may be implemented using a number of heterogeneous processor systems in which a main processor is present with secondary processors on a single chip. As another illustrative example, processor unit 2004 may be a symmetric multi-processor system containing multiple processors of the same type.

Memory 2006 and persistent storage 2008 are examples of storage devices 2016. A storage device is any piece of hardware that is capable of storing information, such as, for example, without limitation, data, program code in functional form, and/or other suitable information either on a temporary basis and/or a permanent basis. Storage devices 2016 may also be referred to as computer readable storage devices in these examples. Memory 2006, in these examples, may be, for example, a random access memory or any other suitable volatile or non-volatile storage device. Persistent storage 2008 may take various forms, depending on the particular implementation.

For example, persistent storage 2008 may contain one or more components or devices. For example, persistent storage 2008 may be a hard drive, a flash memory, a rewritable optical disk, a rewritable magnetic tape, or some combination of the above. The media used by persistent storage 2008 also may be removable. For example, a removable hard drive may be used for persistent storage 2008.

Communications unit 2010, in these examples, provides for communications with other data processing systems or devices. In these examples, communications unit 2010 is a network interface card. Communications unit 2010 may provide communications through the use of either or both physical and wireless communications links.

Input/output (I/O) unit 2012 allows for input and output of data with other devices that may be connected to data processing system 2000. For example, input/output (I/O) unit 2012 may provide a connection for user input through a keyboard, a mouse, and/or some other suitable input device. Further, input/output (I/O) unit 2012 may send output to a printer. Display 2014 provides a mechanism to display information to a user.

Instructions for the operating system, applications, and/or programs may be located in storage devices 2016, which are in communication with processor unit 2004 through communications fabric 2002. In these illustrative examples, the instructions are in a functional form on persistent storage 2008. These instructions may be loaded into memory 2006 for execution by processor unit 2004. The processes of the different embodiments may be performed by processor unit 2004 using computer implemented instructions, which may be located in a memory, such as memory 2006.

These instructions are referred to as program code, computer usable program code, or computer readable program code that may be read and executed by a processor in processor unit 2004. The program code in the different embodiments may be embodied on different physical or computer readable storage media, such as memory 2006 or persistent storage 2008.

Program code 2018 is located in a functional form on computer readable media 2020 that is selectively removable and may be loaded onto or transferred to data processing system 2000 for execution by processor unit 2004. Program code 2018 and computer readable media 2020 form computer program product 2022 in these examples. In one example, computer readable media 2020 may be computer readable storage media 2024 or computer readable signal media 2026. Computer readable storage media 2024 may include, for example, an optical or magnetic disk that is inserted or placed into a drive or other device that is part of persistent storage 2008 for transfer onto a storage device, such as a hard drive, that is part of persistent storage 2008. Computer readable storage media 2024 may also take the form of a persistent storage 2008, such as a hard drive, a thumb drive, or a flash memory, that is connected to data processing system 2000. In some instances, computer readable storage media 2024 may not be removable from data processing system 2000.

Alternatively, program code 2018 may be transferred to data processing system 2000 using computer readable signal media 2026. Computer readable signal media 2026 may be, for example, a propagated data signal containing program code 2018. For example, computer readable signal media 2026 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, program code 2018 may be downloaded over a network to persistent storage 2008 from another device or data processing system through computer readable signal media 2026 for use within data processing system 2000. For instance, program code stored in a computer readable storage medium in a server data processing system may be downloaded over a network from the server to data processing system 2000. The data processing system providing program code 2018 may be a server computer, a client computer, or some other device capable of storing and transmitting program code 2018.

The different components illustrated for data processing system 2000 are not meant to provide architectural limitations to the manner in which different embodiments may be implemented. The different illustrative embodiments may be implemented in a data processing system including components in addition to or in place of those illustrated for data processing system 2000. Other components shown in FIG. 20 can be varied from the illustrative examples shown. The different embodiments may be implemented using any hardware device or system capable of running program code. As one example, the data processing system may include organic components integrated with inorganic components and/or may be comprised entirely of organic components excluding a human being. For example, a storage device may be comprised of an organic semiconductor.

In another illustrative example, processor unit 2004 may take the form of a hardware unit that has circuits that are manufactured or configured for a particular use. This type of hardware may perform operations without needing program code to be loaded into a memory from a storage device to be configured to perform the operations.

For example, when processor unit 2004 takes the form of a hardware unit, processor unit 2004 may be a circuit system, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, programmable array logic, a field programmable logic array, a field programmable gate array, and other suitable hardware devices. With this type of implementation, program code 2018 may be omitted because the processes for the different embodiments are implemented in a hardware unit.

In still another illustrative example, processor unit 2004 may be implemented using a combination of processors found in computers and hardware units. Processor unit 2004 may have a number of hardware units and a number of processors that are configured to run program code 2018. With this depicted example, some of the processes may be implemented in the number of hardware units, while other processes may be implemented in the number of processors.

As another example, a storage device in data processing system 2000 is any hardware apparatus that may store data. Memory 2006, persistent storage 2008, and computer readable media 2020 are examples of storage devices in a tangible form.

In another example, a bus system may be used to implement communications fabric 2002 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 2006, or a cache, such as found in an interface and memory controller hub that may be present in communications fabric 2002.

Data processing system 2000 may also include associative memory 2028. Associative memory 2028 may be termed a content-addressable memory. Associative memory 2028 may be in communication with communications fabric 2002. Associative memory 2028 may also be in communication with, or in some illustrative embodiments, be considered part of storage devices 2016. While one associative memory 2028 is shown, additional associative memories may be present. Associative memory 2028 may be a non-transitory computer readable storage medium for use in implementing instructions for any computer-implemented method described herein.

The different illustrative embodiments can take the form of an entirely hardware embodiment, an entirely software embodiment, or an embodiment containing both hardware and software elements. Some embodiments are implemented in software, which includes but is not limited to forms such as, for example, firmware, resident software, and microcode.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible apparatus that can contain, store, communicate, propagate, or transport the program for use by or in connection with the instruction execution system, apparatus, or device.

The computer usable or computer readable medium can be, for example, without limitation an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example without limitation, physical or wireless.

A data processing system suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories which provide temporary storage of at least some computer readable or computer usable program code to reduce the number of times code may be retrieved from bulk storage during execution of the code.

Input/output or I/O devices can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems or remote printers or storage devices through intervening private or public networks. Non-limiting examples of modems and network adapters are just a few of the currently available types of communications adapters.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An X-ray leak detector comprising:
   an X-ray generator for generating X-rays that strike a target area;
   a shield disposed in front of the X-ray generator, the shield configured to block X-rays backscattered from the target area;
   a first object disposed behind the shield relative to the target area; and
   an X-ray fluorescent Q-dot solution disposed on the first object, the X-ray fluorescent Q-dot solution configured to fluoresce with a visible light when X-rays strike the X-ray fluorescent Q-dot solution.

2. The X-ray leak detector of claim 1, further comprising:
   a camera operatively disposed with respect to the first object such that the camera can detect the visible light resulting from fluorescence of the X-ray fluorescent Q-dot solution.

3. The X-ray leak detector of claim 2, further comprising:
   a computer that stores an image of the visible light and analyzes the visible light to identify a presence of X-rays on the target area.

4. The X-ray leak detector of claim 1, further comprising:
   a second object disposed behind the shield relative to the target area, and further disposed opposite the first object relative to the X-ray generator; and
   a second X-ray fluorescent Q-dot solution disposed on the second object, the second X-ray fluorescent Q-dot solution configured to fluoresce with the visible light when X-rays strike the second X-ray fluorescent Q-dot solution.

5. The X-ray leak detector of claim 4, wherein the first object is disposed to receive first X-rays leaked from a collimator of the X-ray generator and the second object is disposed to receive second X-rays leaked from a location where a cable exits from the X-ray generator.

6. A method of detecting X-ray leaks from an X-ray leak detector, the method comprising:
   generating X-rays from an X-ray generator, wherein the X-rays strike a target area;
   placing a shield disposed in front of the X-ray generator, wherein placing the shield comprises blocking X-rays backscattered from the target area;
   placing an X-ray fluorescent Q-dot solution on a first object disposed behind the shield relative to the target area, the X-ray fluorescent Q-dot solution configured to fluoresce with a visible light when X-rays strike the X-ray fluorescent Q-dot solution.

7. The method of claim 6, further comprising:
   detecting, with a camera operatively disposed with respect to the first object, the visible light resulting from fluorescence of the X-ray fluorescent Q-dot solution.

8. The method of claim 7, further comprising:
   storing, at a computer, an image of the visible light; and
   analyzing, by the computer, the visible light to identify a presence of X-rays on the target area.

9. The method of claim 6, further comprising:
   placing a second X-ray fluorescent Q-dot solution on a second object, the second object disposed behind the shield relative to the target area, and further disposed opposite the first object relative to the X-ray generator, the second X-ray fluorescent Q-dot solution configured to fluoresce with the visible light when X-rays strike the second X-ray fluorescent Q-dot solution.

10. The method of claim 9, wherein placing an X-ray fluorescent Q-dot solution on a first object comprises disposing the first object to receive first X-rays leaked from a collimator of the X-ray generator, and wherein placing a second X-ray fluorescent Q-dot solution on a second object comprises disposing the second object to receive second X-rays leaked from a location where a cable exits from the X-ray generator.

11. The method of claim 6, wherein placing an X-ray fluorescent Q-dot solution on a first object comprises using an aerosol device to spray a surface of the first object.

12. An X-ray monitor comprising:
   an X-ray measuring tool comprising:
      a housing;
      a sensor target area on the housing and configured to receive an X-ray flux; and
      an X-ray detector disposed inside the housing and configured to measure the X-ray flux; and
   an X-ray fluorescent Q-dot solution disposed on the sensor target area, the X-ray fluorescent Q-dot solution configured to fluoresce with a visible light when X-rays strike the X-ray fluorescent Q-dot solution.

13. The X-ray monitor of claim 12, wherein the X-ray fluorescent Q-dot solution further extends past and surrounds the sensor target area.

14. The X-ray monitor of claim 13, further comprising:
a camera disposed to monitor the visible light; and
a computer connected to the camera, wherein the computer is configured to determine whether an expected amount of X-ray flux is entering the sensor target area based on a characterization of the visible light.

15. The X-ray monitor of claim 14, further comprising:
a mechanism connected to the computer, the mechanism configured to adjust an orientation of the X-ray measuring tool, and wherein the computer is further configured to command the mechanism to adjust the orientation based on the characterization such that a desired amount of X-ray flux is entering the sensor target area.

16. A method of using an X-ray monitor, the X-ray monitor comprising: an X-ray measuring tool comprising: a housing; a sensor target area on the housing and configured to receive an X-ray flux; and an X-ray detector disposed inside the housing and configured to measure the X-ray flux; and an X-ray fluorescent Q-dot solution disposed on the sensor target area; the method comprising:
pointing the X-ray monitor towards a source of X-rays, whereby the X-ray fluorescent Q-dot solution fluoresces with a visible light when the X-rays strike the X-ray fluorescent Q-dot solution; and
adjusting an orientation of the X-ray monitor to increase a luminescence of the visible light from the sensor target area, whereby an increased flux of the X-rays will pass through the sensor target area into the X-ray detector.

17. The method of claim 16, wherein the X-ray fluorescent Q-dot solution further extends past and surrounds the sensor target area.

18. The method of claim 17, further comprising:
monitoring the visible light with a camera; and
determining, using a computer connected to the camera, whether an expected amount of X-ray flux is entering the sensor target area based on a characterization of the visible light.

19. The method of claim 18, further comprising:
using a mechanism, connected to the computer, to adjust an orientation of the X-ray measuring tool based on the characterization such that a desired amount of X-ray flux is entering the sensor target area.

20. The method of claim 16 further comprising:
spraying the X-ray fluorescent Q-dot solution onto the sensor target area using an aerosol device.

* * * * *